United States Patent [19]

Schreiber et al.

[11] 4,381,774
[45] May 3, 1983

[54] SAFETY SYSTEM FOR BREATHING APPARATUS

[76] Inventors: Peter J. Schreiber, Box 74, R.D. 1, Zionsville, Pa. 18092; Joachim G. M. Schreiber, Babcock Tower Apartments, Apt. 6-D, 270 Babcock St., Boston, Mass. 02215

[21] Appl. No.: 213,283

[22] Filed: Dec. 5, 1980

Related U.S. Application Data

[63] Continuation-in-part of Ser. No. 86,196, Oct. 18, 1979, abandoned.

[51] Int. Cl.³ .............................................. A61M 17/00
[52] U.S. Cl. ......................... 128/202.22; 128/204.21; 128/205.23
[58] Field of Search ..................... 128/202.22, 204.21, 128/204.23, 205.23

[56] References Cited

U.S. PATENT DOCUMENTS

| 3,333,584 | 8/1967 | Andreason et al. | 128/202.22 |
| 3,480,005 | 11/1969 | Edwards | 128/680 |
| 3,877,467 | 4/1975 | Plicchi | 128/202.22 |
| 3,906,934 | 9/1975 | Haverland | 128/202.22 |
| 4,148,313 | 4/1979 | Bird et al. | 128/204.23 |
| 4,187,842 | 2/1980 | Schreiber | 128/202.22 |

Primary Examiner—Kyle L. Howell
Assistant Examiner—John C. Hanley

[57] ABSTRACT

A safety system for use in a breathing system of an anesthesia apparatus including a gas supply circuit and re-breathing or counter lung circuit. The safety system includes pneumatically operated switches, battery-powered monitoring circuitry and alarm circuitry. The alarm circuitry is coupled to the monitoring circuitry to provide an alarm signal in the event that gas pressure in the breathing circuit exceeds a threshold level for a predetermined period of time, irrespective of the mode of operation of the apparatus. The pneumatically operated switches are arranged to minimize battery drainage during operation.

9 Claims, 2 Drawing Figures

SAFETY SYSTEM FOR BREATHING APPARATUS

BACKGROUND OF THE INVENTION

This invention relates generally to anesthesia machines and more particularly to safety devices therefore, and is a Continuation-In-Part of my co-pending United States Application Ser. No. 086,196 filed on Oct. 18, 1979 now abandoned and whose disclosure is incorporated by reference herein.

As is known, commercially available rebreathing type anesthesia machines basically comprise means for supplying fresh gas, i.e., oxygen and an anesthesia gas, through conduits for introduction into the patient's lungs and rebreathing means in the form of an inflatable component to serve as a counterlung. Typical of such counterlungs are inflatable breathing bags and ventilator bellows. The rebreathing means is coupled through a $CO_2$ absorber or cannister to the fresh gas supply. An inspiratory valve is coupled to the gas supply means and to the rebreathing means to enable gas from the fresh gas supply and the counterlung to flow into the patient's lungs during the inspiratory phase of a breathing cycle. An expiratory valve enables the gas expelled from the patient's lungs to flow to the counterlung. A valve, commonly called an adjustable pressure limiting (APL) valve is coupled to the rebreathing means and arranged to vent expired gas out of the system when the gas pressure slightly exceeds the inflating pressure of the breathing bag.

Rebreathing type anesthesia apparatus may be operated in one of three different modes of operation, namely, spontaneously breathing, artificial ventilation by means of manual bag squeezing and artificial ventilation by the use of a powered ventilator.

During spontaneous breathing, the lungs of the patient form the active member for moving the gas within the system while the breathing bag acts as a passive flexible member. A selector valve is used to connect the patient's breathing system to the rebreathing bag. During the inspiratory phase of spontaneous breathing, the patient expands his thorax, thereby generating a subatmospheric pressure of approximately 1 cm of water, which draws gas from the partially or completely filled rebreathing bag, via the selector valve, the carbon dioxide absorber and the inspiratory valve, into the lungs. During the same inspiratory period, the fresh gas supply means feeds a continuing gas flow into the system. This continuing flow joins the gas from the rebreathing bag on its way to the patient's lungs. The amount of fresh gas provided into the system is determined by the anesthesiologist, but must at least contain the metabolic oxygen requirements of the patient and the volume of anesthesic gases or vapors which is required to maintain anesthesia. Based on safety considerations, the amount of gas delivered into the system is usually many times the amount of volume per minute actually required by the oxygen consumption and anesthesia needs of the patient. If the breathing circuit includes various accessories, such as, humidifiers, bacteria, filters, etc., the resistance of the breathing circuit is increased and a higher sub-atmospheric pressure may be produced by the patient during the inspiratory phase, with the maximum acceptable sub-atmospheric pressure being approximately 2 cm of water.

At the end of the inspiratory phase, there is a short pause during which the breathing circuit pressure is atmospheric. As the expiratory phase commences, the pressure begins to increase above atmospheric pressure. During the expiratory phase, the patient exhales from his lungs, via the expiratory valve and the selector valve, into the rebreathing bag.

Inasmuch as fresh gas is delivered into the system by the fresh gas supply, during both the inspiratory and expiratory phases, the total amount of gas in the system is greater toward the end of the expiratory cycle. Accordingly, at a certain point in the expiratory phase, the rebreathing bag will be filled while the pressure in the breathing system continues to increase until the APL valve opens. The APL valve, when open, serves a bleed off gas into a gas scavaging system to prevent the build up of excess pressure in the breathing system.

APL valves vary in their design and specific performance. Some APL valves are spring loaded devices which remain closed until subjected to a predetermined threshold pressure at which time they open fully. Other APL valves are of the resistance type wherein the flow resistance of the valve is established by the adjustment of a variable orifice. Such valves constantly bleed off gas from the breathing system. Irrespective of the type of APL valve used, the valve is adjusted so that it operates to bleed off gas from the breathing system cycle, each cycle to prevent the pressure therein from exceeding slightly more than the inflating pressure of the counterlung, e.g., bag. To that end, the APL valve may be set to prevent the pressure from exceeding 1–3 cm of water, depending upon conditions. Thus, the amount of gas expelled through the APL valve depends upon and is approximately equal to the amount of fresh gas delivered from the anesthesia machine during the same period of time. While anesthesia apparatus include pressure gauges for displaying system pressure, due to the extremely low pressure setting of the APL valve, the very slight pressure fluctuations during spontaneous breathing are normally not observable at the pressure gauge.

During artificial ventilation by means of bag squeezing, the selector valve of the apparatus is set in the same position as during spontaneous breathing, namely, to connect the rebreathing bag to the breathing system.

In the bag squeezing operation, in order to perform the ventilation, the pressure setting of the APL valve is increased substantially to a level equal to the maximum of inspiratory pressure required to ventilate the patient adequately. Such a pressure setting may depend on the conditions of airway resistance and lung compliance.

Operation of the breathing system during bag squeezing is as follows: the partial or completely filled rebreathing bag is squeezed manually, thus increasing the pressure within the breathing system. The increased pressure in the system creates a flow of gas from the system through the airway to the lungs through the same path as occurs during the inspiratory phase of spontaneous breathing, with the pressure in the system being always higher than the pressure in the lungs during the inspiratory phase (depending on the airway resistance).

In anesthesia machines using spring loaded APL valves, the pressure in the system rises until the opening pressure of the APL valve is reached and thereafter the gas is expelled or bled through the valve into a scavenging system. This precludes further increase in breathing system pressure.

During either the spontaneous breathing or artificial ventilation by bag squeezing modes of operation, the expiratory phase results from the simple release of pressure on the rebreathing bag. This permits the patient to spontaneously exhale from his lungs, via the expiratory valve and the selector valve into the rebreathing bag.

During artificial ventilation employing a ventilator, e.g., bellows, operation of the system is as follows: the selector valve is set so that the bellows of the ventilator is connected to the breathing system and the rebreathing bag disconnected from the breathing system. In this mode of operation, the bellows is contracted, thus delivering gas via the selector valve, the $CO_2$ absorber and the inspiratory valve to the patient's lungs. In order to bleed excess gas from the ventilator, the ventilator includes a relief valve which is closed by means of pressure in a pilot line leading from the ventilator.

As in other modes of operation, the flow of fresh gas is delivered continuously into the patient breathing system. The continuing fresh gas flow joins the inspiratory gas delivered from the bellows on its way to the lungs of the patient. With the beginning of the expiratory phase, the pressure on the bellows is released, thus permitting the bellows to expand and the patient to exhale from his lungs, via the expiratory valve and the selector valve, into the ventilator bellows. At the same time, the pilot pressure which closes the ventilator relief valve during the inspiratory cycle decreases to zero and permits the ventilator relief valve to be opened by the higher pressure within the breathing system. Thus, an amount of fresh gas equal to the amount delivered by the anesthesia machine during the inspiratory-expiratory cycle is expelled into the scavenger system of the anesthesia machine.

In both types of artificial ventilation, i.e., manual bag squeezing or automatic ventilation by a bellows, it is absolutely necessary for the operator to insure that there is produced a positive pressure in the breathing system in order to ventilate the patient's paralyzed lungs. Positive pressure in the lungs, however, retards the return of venous blood flow, which may leave vital organs, like the brain, without necessary oxygen supply, thereby exposing the patient to severe injury. Thus, during operation of an anesthesia machine in either the spontaneous breathing mode of operation or in either of the two artificial ventilation modes of operation, it is of considerable importance that an anesthesia machine be operated so that it does not maintain positive pressure for an abnormally long period of time. In normal operation, the alternating pressure changes during the inspiratory and expiratory phases permit the venous return of blood during periods of low pressure.

Various accidents have been reported using ventilating apparatus due to operator error resulting in the production of continuing positive pressure in the system. For example, one typical operator-caused type of accident occurs as follows: During surgery while a patient's lungs are disabled and the machine is operated in the bellows ventilating mode, the operator closes the APL valve. At the end of the surgical procedure when the patient regains his capability to spontaneous breathing, the operator switches the selector valve back to the setting for connecting the rebreathing bag, but due to oversight or misjudgment, the anesthesiologist or operator neglects to open the APL valve. This results in excessive pressure in the system (since fresh gas is being continuously delivered into the system and cannot escape through the closed valve) and patient injury may result.

Penlon Ltd. of Radley Road, Abington, Oxon OX143PH England manufactures an IDP Pressure Failure Alarm which is a self-contained battery powered alarm designed for patient protection against ventilator failure or circuit disconnection during Intermittent Positive Pressure Ventilation (IPPU). When the alarm is connected to the breathing circuit of an anesthesia apparatus, it produces an audible and visual warning if the pressure in the breathing circuit fails to increase through a set level, e.g., 7.5-12.5 cm of water, and then decreases through the set level within a predetermined period of time.

While the Penlon device appears suitable for its intended purposes during either artificial mode of ventilation, it is incapable of use during the spontaneous mode of operation. This drawback is due to the fact that the Penlon device will produce an alarm at all times during spontaneous breathing since the pressure fluctuations during spontaneous breathing are substantially below the threshold of the Penlon device.

In U.S. Pat. No. 3,333,584, there is disclosed a pressure breathing monitor which like the aforementioned Penlon device, appears incapable of use in spontaneous breathing conditions.

In our aforementioned parent patent application, there is disclosed and claimed a safety system for anesthesia apparatus, which produces an express warning to the operator of the existence of continuous pressure within the patient breathing system. To accomplish that end, the system includes means for monitoring the pressure within the patient breathing circuit and for providing a warning signal to the operating personnel in the event that the system pressure is sustained for a predetermined period of time and irrespective of the mode of operation of the anesthesia apparatus.

Those and other objects of the invention disclosed and claimed in that application are achieved by providing safety means for use in an anesthesia apparatus. The anesthesia apparatus includes a breathing circuit comprising gas supply means and rebreathing means comprising alternately selectable powered ventilator means and rebreathing bag means and means for selecting the rebreathing means. The apparatus is arranged for supplying gas to a spontaneously breathing patient from the breathing bag means during a first mode of operation or to artificially ventilate the patient by manually squeezing said bag means during a second mode of operation or to artificially ventilate the patient automatically by powered ventilator means during a third mode of operation. The gas supply means and the selected rebreathing means are connected together by the selecting means for enabling gas from the gas supply means and gas from the selected rebreathing means to flow together at a first point. Conduit means are coupled to the lungs of the patient. Inspiratory valve means are coupled to the gas supply means and the rebreathing means for enabling gas from the first point to flow downstream through the conduit means to the patient's lungs. Expiratory valve means are coupled between the conduit means and the rebreathing means for enabling gas from the first point to flow downstream through the conduit means to the patient's lungs. The expiratory valve means are coupled between the conduit means and the rebreathing means for enabling gas to flow downstream from the patient's lungs through the conduit means to the selected rebreathing means. Pressure release means are provided to venting gas out of the breathing circuit. The safety means comprises pressure sensing means for monitoring the gas pressure downstream of the first point and means coupled to the pressure sensing means and responsive thereto for providing an alarm signal only in the event that the gas pressure monitored exceeds a predetermined value for a predetermined period of time and irrespective of the mode of operation of said apparatus.

The instant invention comprises an improvement over the invention disclosed and claimed in our aforementioned parent patent application by providing a safety system which exhibits all of the features and advantages of that invention and which also ensures that there is no excessive power drain on the electrical power source for the safety system.

OBJECTS OF THE INVENTION

Accordingly, it is a general object of the instant invention to provide in anesthesia apparatus, electrically powered means for monitoring the pressure within the patient breathing circuit and for providing a warning signal to operating personnel in the event that the system pressure is sustained for a predetermined period of time and which means conserves electric power.

That and other objects of the instant invention are achieved by providing safety means for use in an anesthesia apparatus. The anesthesia apparatus has a breathing circuit comprising gas supply means and rebreathing means comprising alternately selectable powered ventilator means and rebreathing bag means and means for selecting the rebreathing means. The apparatus is arranged for supplying gas to a spontaneously breathing patient using the bag means during a first mode of operation or to artificially ventilate the patient by manually squeezing the bag means during a second mode of operation or to artificially ventilate the patient automatically by the powered ventilator during a third mode of operation. The bag means is selected by the selecting means during either said first or second mode of operation. The powered ventilator means is selected by the selecting means during the third mode of operation. The gas supply means and the selected rebreathing means are connected together by the selecting means for enabling gas from said supply means and from the selected rebreathing means to flow together at a first point. Conduit means are coupled to the lungs of a patient. Inspiratory valve means are connected to the gas supply means and to the selected rebreathing means for enabling gas from the first point to flow downstream through the conduit means to the lungs. The expiratory valve means are coupled between the conduit means and the rebreathing means for enabling gas to flow downstream from the lungs through the conduit means to the selected rebreathing means. Pressure relief means are provided for venting gas out of the selected rebreathing means. The improvement comprises first pressure sensing means for monitoring the gas pressure downstream of the first point and battery operated means responsive thereto for providing an alarm signal only in the event that the pressure monitored exceeds a first predetermined value for a predetermined period of time irrespective of the mode of operation of the apparatus. Second pressure sensing means are provided to disconnect said battery from said means responsive in the event that the pressure monitored exceeds a second predetermined value, said second predetermined value being less than said first predetermined value and higher than the maximum pressure existing during normal spontaneous breathing conditions of said patient.

Other objects of many of the attendant advantages of the instant invention will be readily appreciated as the same becomes better understood by reference to the following detailed description when considered in connection with the accompanying drawing wherein:

DETAILED DESCRIPTION OF THE PREFERRED EMBODIMENT

Figure 1:
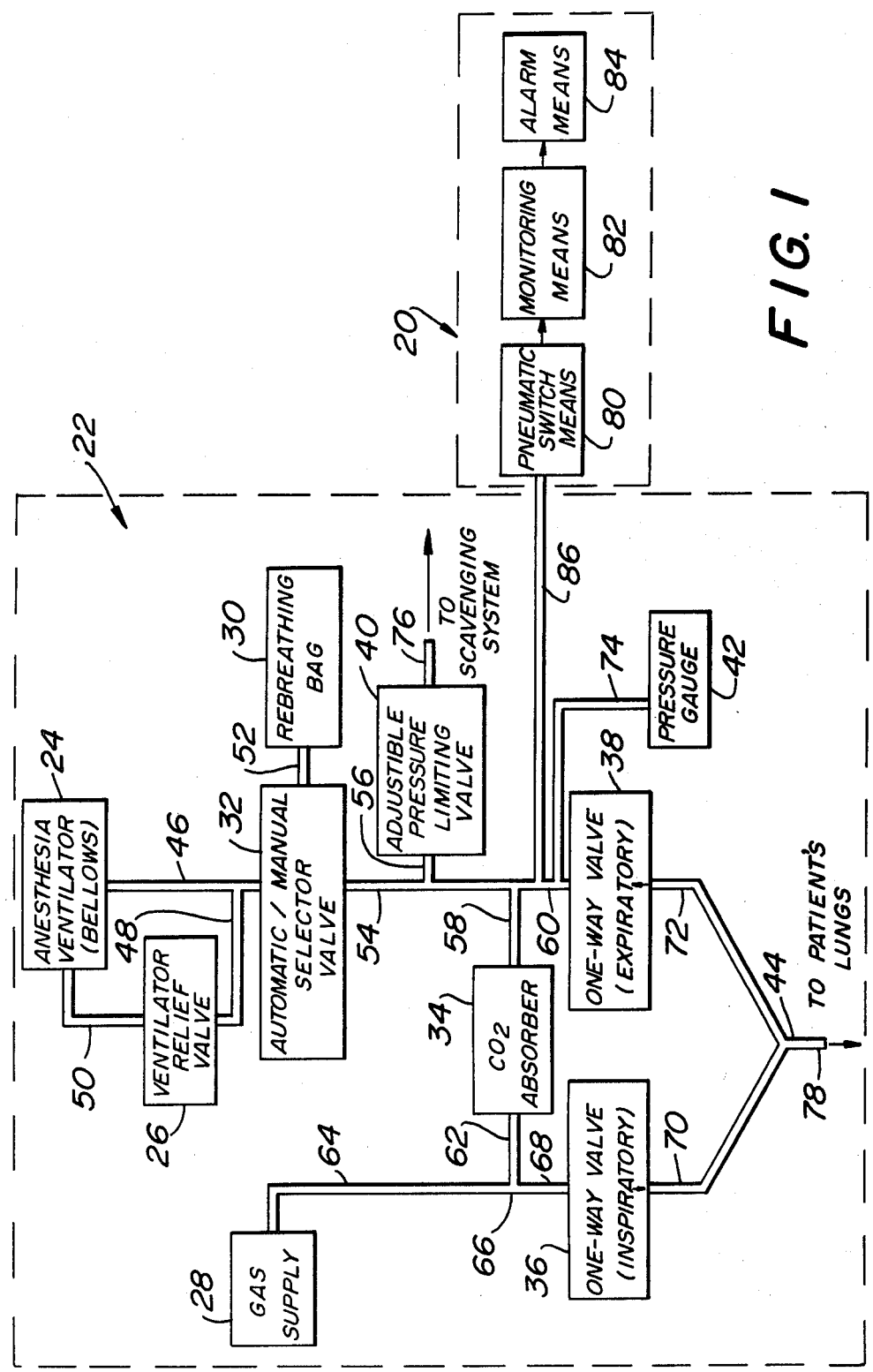
FIG. 1 is a functional block diagram of the safety system of the invention connected to a conventional rebreathing type anesthesia machine.

Referring now to the various figures of the drawing wherein like reference, refer to like parts, there is shown at 20 in FIG. 1 a safety system in accordance with the instant invention connected to a conventional anesthesia machine 22.

The anesthesia machine 22 basically comprises an anesthesia ventilator 24, including a bellows, a ventilator relief valve 26, fresh gas supply means 28, a rebreathing bag 30, an automatic/manual selector valve 32, a dual $CO_2$ absorber 34, a one-way inspiratory valve 36, a one-way, expiratory valve 38, an adjustable pressure limiting (APL) valve 40, a system pressure gauge 42 and a "Y" piece 44. The bellows of the ventilator is connected, via a gas line 46, to the automatic/manual selector valve 32. The ventilator relief valve is connected, via a gas line 48 to line 46 and, via a pilot line 50, to the ventilator 24. The automatic/manual selector valve 32 is connected, via a gas line 52, to the rebreathing bag 30. A gas line 54 is connected to the outlet of the automatic/manual selector valve 32, to an inlet gas line 56 of the APL valve 40, to an inlet gas line 58 of the $CO_2$ absorber 34 and to outlet gas line 60 of the expiratory valve 38. The outlet line 62 of the $CO_2$ absorber 34 is connected to the outlet gas line 64 of the gas supply 28. Gas line 62 and 64 merge together at point 66, which serves as the inlet 68 to the inspiratory valve 36. The outlet of the inspiratory valve 36 is connected, via gas line 70, to one leg of the "Y" piece 44. The other leg of the "Y" piece 44 is connected, via a gas line 72 to the input of the expiratory valve 38. The "Y" piece includes an outlet 78 for connection, e.g., via a mask, to the patient's respiratory system. The system pressure gauge 42 is connected, via a gas line 74, to the outlet line 60. The outlet of the APL valve is connected, via gas line 76 to the machine's scavenging system (not shown).

Operation of the apparatus 20 is as follows: During artificial ventilation by manual bag squeezing, the automatic/manual selector valve 32 is set so that the line 52 is connected to line 54 and disconnected from line 46 of the ventilator. The APL valve 40 is adjusted to enable the bag 30 to fill up so that the breathing system pressure just exceeds the bag filling pressure. During the inspiratory phase, the squeezing of the rebreathing bag 30 by the machine operator causes gases in the bag to pass through line 52 and valve 32 into line 54. The gases in line 54 flow through inlet line 58 into the $CO_2$ absorber where carbon dioxide is absorbed and the remaining gas flow through outlet 62 for merger at 66 with fresh gas supplied, via line 64, from the fresh gas supply 28. The combined gases flow through input line 68, one-way valve 36, outlet line 70 to "Y" piece 44 for passage, via conduit 78, to the patient's lungs. In machines using a spring loaded type APL valve, when the pressure produced by the manual squeezing of the rebreathing bag exceeds the pressure setting of the valve, excess gas is bled from the rebreathing bag through the valve to line 76 and hence to the scavenging system. In machines using resistance type APL valve, the valve is adjusted to continuously bleed gases from the rebreathing system during the bag squeezing so as to preclude the pressure from building up beyond the desired level.

During the expiratory phase of ventilation by manual bag squeezing, the operator releases the manual pressure or squeeze applied to the bag. This action permits the patient to spontaneously exhale from his lungs, via conduit 78, inlet line 72, expiratory valve 38, outlet line 60, line 54, automatic/manual selector valve 32, and line 52, into the rebreathing bag 30.

Thus, during ventilation by manual bag squeezing, gas is expelled at the end of the expiratory cycle (for spring loaded type APL valves) and all during the inspiratory cycle (for resistance type APL valves) and the pressure in the system decreases to atmospheric pressure when the rebreathing bag 40 is released by the operator. The system pressure gauge 42 displays the system pressure at all times for use by the operator.

During artificial ventilation by use of a powered ventilator, e.g., bellows, the system 22 operates as follows: The automatic/manual selector valve is switched to the position to connect input line 46 from the ventilator to line 54 and to disconnect line 54 from line 52 and hence the rebreathing bag 30. The APL valve 40 is then closed, with its function (i.e., precluding the production of excessive pressure in the system) taken over by the ventilator relief valve 26.

During the inspiratory phase, the bellows is contracted by means, not shown, thus, delivering gases, via line 46 and automatic/manual selector valve 32, into line 54. The gas from line 54 flows through the $CO_2$ absorber and meets the fresh gas in line 64 in the same manner as described heretofore. Accordingly, the gas from the ventilator and the fresh gas supply is fed to the lungs of the patient. During the inspiratory phase, the ventilator relief valve 26 is closed by means of the pressure in the pilot line 50. With the beginning of the expiratory phase, the pressure on the bellows is released, thus permitting the bellows to expand and the patient to spontaneously exhale from his lungs, via the "Y" piece 44, line 72, one-way expiratory valve 38, outlet line 60, line 54, automatic/manual selector valve 32 and line 46, into the ventilator bellows. At the same time, the pilot pressure which closed the ventilator relief valve during the inspiratory cycle decreases to zero pressure and permits the ventilator relief valve 26 to open by the higher pressure within the patient breathing system. Thus, an amount of fresh gas equal to the amount delivered by the machine during the inspiratory-expiratory cycle is expelled by means (not shown) into the scavenger system of the anesthesia machine.

Operation of the apparatus 20 during spontaneous breathing is as follows: The automatic/manual selector valve 32 is set so that the line 52 is connected to line 54 and disconnected from line 46 of the ventilator. The APL valve 40 is adjusted to enable the bag 30 to fill up so that the breathing system pressure just exceeds the bag filling pressure. During the inspiratory phase, the patient expands his thorax, thereby generating a slight sub-atmospheric pressure which draws gases in the bag to pass through line 52 and valve 32 into line 54. The gases in line 54 flow through inlet line 58 into the $CO_2$ absorber where carbon dioxide is absorbed and the remaining gas flow through outlet 62 for merger at 66 with fresh gas supplied, via line 64, from the fresh gas supply 28. The combined gases flow through input line 68, one-way valve 36, outlet line 70 to "Y" piece 44 for passage, via conduit 78 to the patient's lungs. In the expiratory phase, the patient exhales the gases from his lungs into the "Y" piece. The expelled gases flow through the expiratory valve 38 into line 60, through the selector valve 32 to the rebreathing bag 30. The bag commences to fill until the pressure in line 54, e.g., 2 cm of water, exceeds the pressure setting of valve 40, whereupon the excess gas is bled into the scavenging system. In machines using resistance type APL valve, the valve is adjusted to continuously bleed gases from the rebreathing system during the bag inflation to preclude the pressure from building up beyond the desired level.

As noted heretofore, with conventional anesthesia machines 22, in the event of operator error, the positive pressure normally occurring during one phase of each operating cycle may continue for an unreasonably long period of time, thereby preventing venous return of blood to the heart and concomitant injury to the patient. While the pressure gauge 42 of the system displays system pressure, the system operator may neglect to notice that the pressure is not varying. This is particularly true in cases where the sustained positive pressure is low level. The safety system 20 of the instant invention is arranged for use with any rebreathing type anesthesia machines to obviate the problems of operator error in the use of the prior art apparatus by providing an express warning signal in the event that positive pressure exists for a predetermined period of time, irrespective of the mode of operation of the device, i.e., spontaneous breathing, artificial ventilation by means of manual bag squeezing or automatic artificial ventilation by means of a powered ventilator (bellows).

The safety system 20 basically comprises pneumatic switch means 80, monitoring means 82, and alarm means 84 and is preferably powered by a self-contained electrical power source, e.g., 9-volt battery (not shown). The pneumatic switch means 80 comprises two pneumatically operated electrical switch devices 150 and 152, each having a pneumatic input which is connected, via a pilot line 86, to communicating gas lines 54, 58 and 60. Each switch 150 and 152 includes a pair of electrical contacts (to be described later) which are arranged to close in the event that the pressure in pilot line 86 exceeds the respective predetermined threshold level of each switch.

It must be pointed out at this juncture that while the pilot line 86 is shown in FIG. 1 connected to line 54, it may be connected to various other points in the system downstream of the point 66 at which the fresh gas flow meets the gas flow from the rebreathing means.

The switch 150 serves as means for automatically disconnecting the safety system from the battery when the pressure in the pilot line 86 is below a first predetermined threshold level. The first predetermined threshold level is slightly in excess of the peak pressure which could reasonably be encountered during normal spontaneous breathing conditions. Since normal spontaneous breathing should not exceed a maximum pressure of 2 or 3 cm of water, the threshold level of switch 150 is set at 5 cm of water. Accordingly, switch 150 ensures that when the anesthesia apparatus is in operation under spontaneous breathing conditions or when the anesthesia apparatus in not being used, the circuitry of system 20 does not drain the power source.

In the event that the pressure in the pilot line 86 exceeds the predetermined threshold level, the contacts switch close to automatically enable the system to detect the existence of excessive positive pressure. That action is accomplished through the operation of switch 152 and the associated monitoring means 82. To that end, switch 152 is arranged to close its contacts whenever the pressure on the pilot line 86 reaches a second predetermined threshold level (the excessive positive pressure level), e.g., 12.5 cm of water. The switch 152 is connected to the monitoring means 82 and is arranged so that upon closure of its contacts, it initiates operation of the monitoring means 82. The monitoring means is, in turn, connected to the alarm means and is arranged to initiate operation of the alarm means 84 in the event that it senses the existence of the excessive positive pressure for a predetermined period of time. Once the alarm means is initiated, it provides both an audible and visual alarm signal to alert operating personnel of the alarm condition.

As will be described in detail later, the monitoring means includes adjustable circuitry for establishing the predetermined period of time that the monitoring means must sense positive pressure before initiating operation of the alarm means. It is preferable when the safety system 20 is used in anesthesia apparatus that the predetermined time period be adjusted or set so as to be just slightly longer than the longest-to-be-expected (e.g., 10 seconds) inspiratory phase of a breathing cycle. This ensures that the system provides a sufficient safety margin to alert operating personnel of the sustenance of positive pressure for longer than the maximum typical breathing cycle, but will not produce a spurious alarm signal (in the event of a slow breathing cycle).

Figure 2:
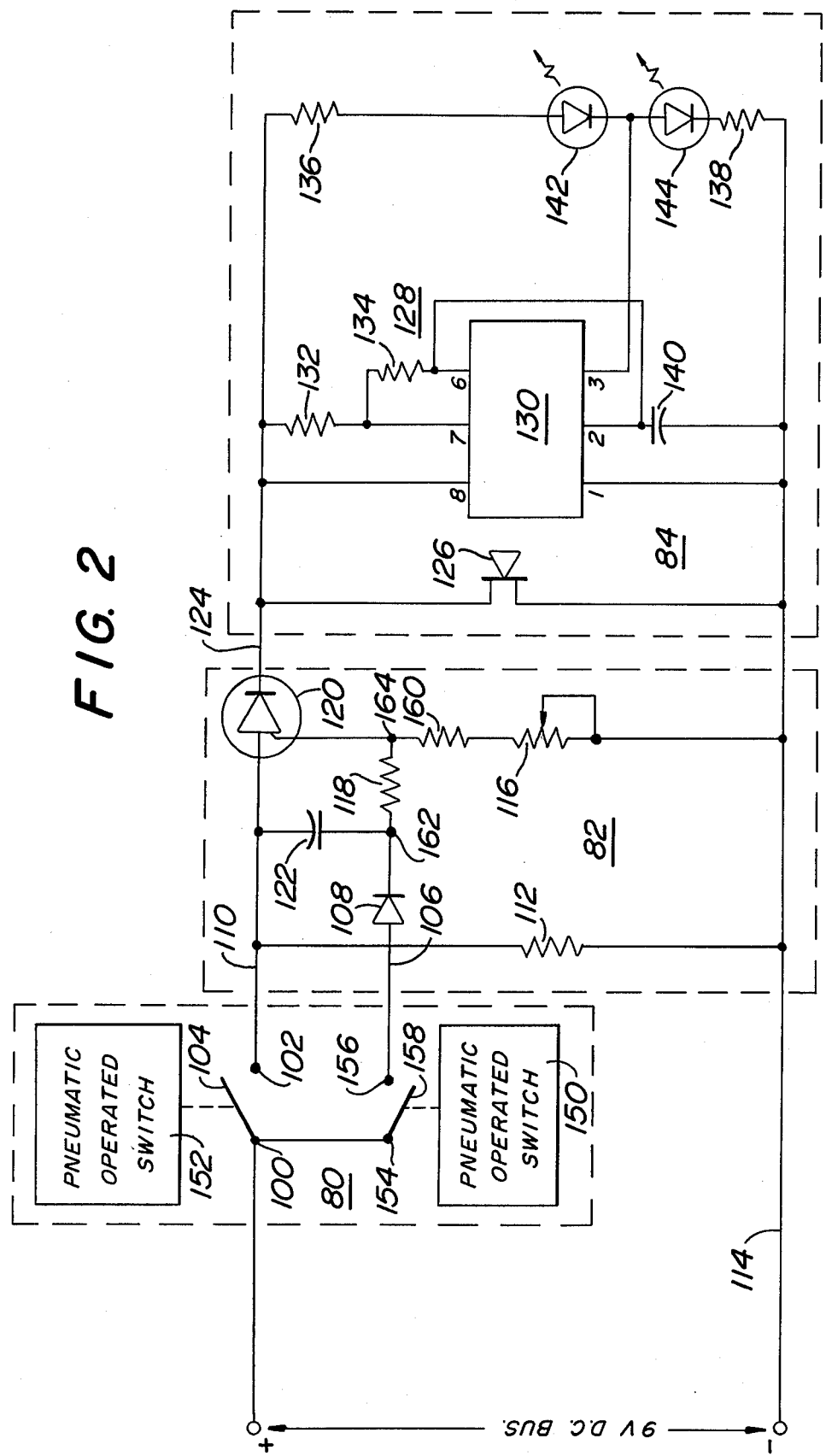
FIG. 2 is a schematic diagram of the means making up the safety system shown in FIG. 1.

Referring now to FIG. 2, the details of the safety system 20 are shown. As can be seen therein, the system 20 includes a positive and negative DC power buses, which are connected to the DC supply, e.g., 9-volt battery, (not shown). The switch 150 includes a pair of contacts 154 and 156 and a movable contactor 158 which closes the contacts when the switch 150 senses that the pressure in line 86 is in excess of the first predetermined threshold pressure, e.g., 5 cm of water. The switch 152 includes a pair of contacts 100 and 102 and a movable contactor 104 which closes contacts 100 and 102 when the switch 152 senses that the pressure in line 86 is in excess of the second predetermined threshold pressure, e.g., 12.5 cm of water.

The contact 154 of switch 150 is connected to the contact 100 of switch 152 and to the positive DC bus. The contact 102 of switch 152 is connected to line 110 which serves as an input line to the monitoring means 82. The contact 156 of switch 150 is connected to line 106. Line 106 is another input line to means 82 and is connected to the anode of a diode 108 in means 82. The line 110 is connected to one side of a resistor 112 in the monitoring means 82. The other side of resistor 112 is connected to the negative DC bus 114. The monitoring means also includes a potentiometer 116. One side of the potentiometer 116 and its wiper arm is connected to negative bus 114 while the other side of the potentiometer 116 is connected to one side of a resistor 160. The other side of resistor 160 is connected to the junction of a resistor 118 and the gate of a PNPN Silicon Programmable Unijunction Transistor 120. The other side of resistor 118 is connected to the junction of one side of capacitor 122 and the cathode of diode 108. The other side of capacitor 122 is connected to the junction of the anode of the unijunction transistor 120, the other side of resistor 112 and line 110. The cathode of the unijunction transistor 120 is connected to line 124.

Lines 124 and 114 serve as the input to the alarm means 84. The alarm means 84 includes an annunciator or speaker 126 and flashing circuitry 128 connected between lines 124 and 114. The flashing circuitry comprises an integrated circuit 130, associated resistors 132, 134, 136 and 138, an associated capacitor 140 and a pair of light emitting diodes 140 and 142. The integrated circuit 130 shown herein is a 555 type device, such as sold by Sygnetics or Texas Instruments. As can be seen, pin 8 of integrated circuit 130 is connected to line 124 while pin 1 of said circuit is connected to line 114. One side of the resistor 132 is connected to the common junction of pin 7 of circuit 130 and to one side of the resistor 134. The other side of the resistor 134 is connected to the common junction of pins 6 and 2 of the integrated circuit 130. Pin 2 of the integrated circuit is also connected to one side of capacitor 140. The other side of capacitor 140 is connected to the bus 114. Pin 3 of circuit 130 is connected to the common junction of the cathode and anode of light emitting diodes 142 and 144, respectively. The resistor 138 is connected between the cathode of diode 144 and the bus 114, while the resistor 136 is connected between the anode of diode 142 and the common junction of one side of resistor 132 and line 124.

The annunciator or speaker 126 of the alarm means 84 provides an audible alarm upon the application of a voltage thereacross, while the visual alarm means 128 causes the light emitting diodes thereof to flash intermittently as the annunciator 126 sounds.

Operation of the safety system is as follows: In the event that the pneumatic operated switch 150 senses pressure in the pilot line 86 is in excess of the first threshold pressure, e.g., 5 cm of water, of the switch, movable contact 158 closes to bridge contacts 154 and 156. This action precharges the capacitor 122 to the potential of the DC supply through the path consisting of the positive DC bus, the closed switch 150, line 106, diode 108, capacitor 122, resistor 112 and the negative DC bus. Should the pressure in line 86 exceed the second predetermined pressure, e.g., 12.5 cm of water, the switch 152 causes its contactor 104 to bridge contacts 100 and 102. This action connects the anode of the unijunction transistor 120 to the positive DC bus and also supplies a positive pulse through the capacitor 122 to the junction 162 between diode 108 and resistor 118. The positive pulse momentarily elevates the potential at the junction 162 to approximately double the DC supply while the potential at the anode of unijunction transistor 120 remains at that of the DC supply. The resistors 118, 160 and 116 form a voltage divider so that the potential at the junction 164 between the resistors 118 and 160 momentarily increases to something less than the potential at junction 162, with the potential at 164 being dependent upon the setting of potentiometer 116. The potential at junction 164, and hence at the gate of unijunction transistor 120 immediately commences to decay, with the rate of decay being established by the setting of potentiometer 116. When the potential at the gate of the unijunction transistor has decayed to a point where it is approximately equal to the potential on the anode, the unijunction transistor commences conduction, thereby applying the positive DC bus potential onto line 124. The DC voltage on line 124 causes the annunciator or speaker 126 to sound audibly while activating integrated circuit 130 to result in the flashing of light emitting diodes 142 and 144. Since the setting of potentiometer 116 establishes the rate of discharge of the capacitor, and hence the conduction point of the unijunction transistor 120, by selecting an appropriate resistance setting for the potentiometer, the time delay between the actuation of switch 152 and the production of an alarm signal is established as desired. As mentioned heretofore, an appropriate time delay is ten seconds since that time period is slightly longer than the longest-to-be-expected inspiratory phase of a breathing cycle.

In the event that the pressure in pilot line 86 drops below the threshold pressure, i.e., 12.5 cm of water, of switch 152 before the unijunction transistor 120 conducts, the switch opens its contacts 100 and 102. This causes the capacitor 122 to begin recharging through the diode 108 and resistor 112. The recharging of capacitor 122 prevents the unijunction transistor from conducting, thereby resetting the monitoring means 82 and preventing the initiation of an alarm signal.

The following table represents component values and identification for a practical embodiment of system 20. However, it must be understood that the system 20 need not be constructed as shown herein so long as it includes means for monitoring breathing system pressure and for providing an alarm signal in the event that such pressure exists for longer than a predetermined period of time, irrespective of the mode of operation of the anesthesia apparatus. Furthermore, while the monitoring means 82 of system 20 is shown connected to alarm means 84 to provide a signal in the event of the detection of a sustained positive pressure, it is clear that the signal from the monitoring means 82 can be utilized by means (not shown) to automatically take some action to relieve the pressure in the breathing system, e.g., open a safety or pressure relief valve in the breathing circuit.

Moreover, while the safety system 20 has been disclosed with reference to the detection of sustained positive pressure, such as could occur by the omission of the operator to open APL valve 40, the system 20 could be modified for use in anesthesia apparatus to prevent patient injury resulting from operator error causing the scavenging system to produce negative pressure in the breathing circuit.

| COMPONENT | VALUE | IDENTIFICATION |
|---|---|---|
| 108 | — | Diode, Texas Instruments, IN914 |
| 112 | 10 K ohms | Resistor |
| 116 | 500 K ohms | Potentiometer, Bourns, 3386 |
| 118 | 33 K ohms | Resistor |
| 120 | — | Unijunction transistor, General Electric, 2N6027 |
| 122 | 47 µf, 20v | Capacitor |
| 126 | — | Annunciator, Mallory, SNP428 |
| 130 | — | Integrated Circuit, Texas Instruments, NE555P |
| 132 | 100 K ohms | Resistor |
| 134 | 680 K ohms | Resistor |
| 136 | 300 ohms | Resistor |
| 138 | 100 ohms | Resistor |
| 140 | 1.0 µf.50v | Tantalum Capacitor |
| 142 | — | Light Emitting Diode, IEE, 211R |
| 144 | — | Light Emitting Diode, IEE, 211R |
| 150 | — | Coventry Corporation, Model 505-3 Mini-switch |
| 152 | — | Coventry Corporation, Model 505-3 Mini-switch |
| 160 | 10 K ohms | Resistor |

As should be appreciated from the foregoing, the safety system 20 of the instant invention is a device which can be readily connected in conventional anesthesia machines for providing an alarm signal to the machine operator in the event that the patient is subjected to sustained or continuing pressure in the breathing system, irrespective of the mode of operation of the machine, i.e., spontaneous breathing, artificial ventilation by manual bag squeezing or automatic artificial ventilation by powered ventilator. By virtue of the adjustability of the monitoring means, the system can be adapted to provide a warning signal in the event that pressure is sustained for any predetermined period of time. This provides great flexibility for use by the anesthesiologist and prevents the occurrence of spurious alarms. The switch means of the system minimizes battery drain by precluding drainage during normal spontaneous breathing conditions or when the anesthesia machine is not being operated.

Without further elaboration, the foregoing will so fully illustrate our invention that others may, by applying current or future knowledge, readily adapt the same for use under various conditions of service.

What is claimed as the invention is:

1. In an anesthesia apparatus having a breathing circuit gas supply means and rebreathing means comprising alternately selectable powered ventilator means and rebreathing bag means and means for selecting said rebreathing means, said apparatus being arranged for supplying gas to a spontaneously breathing patient using said bag means during first mode of operation or to artificially ventilate said patient by manually squeezing said bag means during a second mode of operation or to artificially ventilate said patient automatically by said powered ventilator during a third mode of operation, said bag means being selected by said selecting means during either said first or second mode of operation, said powered ventilator means being selected by said selecting means during said third mode of operation, said gas supply means and said selected rebreathing means being connected together by said selecting means for enabling gas from said supply means and from said selected rebreathing means to flow together at a first point, conduit means coupled to the lungs of a patient, inspiratory valve means connected to said gas supply and said selected rebreathing means for enabling gas from said first point to flow downstream through said conduit means to said lungs, expiratory valve means coupled between said conduit means and said rebreathing means for enabling gas to flow downstream from said lungs through said conduit means to said selected rebreathing means, and pressure relief means for venting gas out of said selected rebreathing means, the improvement comprising a safety system comprising alarm means and monitoring means comprising first pressure responsive switch means for monitoring gas pressure downstream of said first point and for establishing a first threshold pressure in excess of pressures normally encountered during spontaneous breathing but below a level at which patient injury could occur, second pressure responsive switch means for monitoring gas pressure downstream of said first point and for establishing a second threshold pressure greater than or equal to said first threshold pressure but below a level at which patient injury could occur, said first pressure responsive switch means enabling said alarm means only if the pressure monitored exceeds said first threshold pressure, said alarm means, when enabled, being responsive to said second pressure responsive switch means for providing an alarm signal only in the event that the pressure monitored exceeds said second threshold pressure for a predetermined period of time, in all three modes of operation of said apparatus, said first pressure responsive switch means disabling said alarm means whenever the pressure monitored is below said first threshold pressure.

2. The apparatus of claim 1 wherein said predetermined period of time is adjustable.

3. The apparatus of claim 2 wherein said alarm signal is audible.

4. The apparatus of claim 3 wherein said alarm signal is visual.

5. The apparatus of claim 4 wherein said alarm signal is audible and visual.

6. The apparatus of claim 5 wherein said first pressure sensing means comprises a pneumatically operated electrical switch.

7. The apparatus of claim 1 wherein said first pressure sensing switch means comprises a first pneumatically operated electrical switch, wherein said second pressure sensitive switch means comprises a second pneumatically operated electrical switch and wherein monitoring means comprises a capacitor and a transistor coupled thereto, said transistor being arranged to change conduction when the charge on said capacitor reaches a predetermined threshold level to produce said alarm signal.

8. The apparatus of claim 7 wherein said monitoring means also comprises adjustment means for adjusting the discharge rate of said capacitor.

9. The apparatus of claim 1 wherein said system is powered by a self-contained electric power source connected to said system by said first pressure responsive switch means said power source being disconnected from said system by said first pressure responsive switch means whenever the pressure monitored is less than said first threshold value.

* * * * *